United States Patent [19]

Lee et al.

[11] Patent Number: 5,118,853

[45] Date of Patent: Jun. 2, 1992

[54] PROCESSES FOR THE SYNTHESIS OF 3-DISUBSTITUTED AMINOACROLEINS

[75] Inventors: George T. Lee, Bloomfield; Oljan Repic, Randolph, both of N.J.

[73] Assignee: Sandoz Ltd., Basel, Switzerland

[21] Appl. No.: 661,286

[22] Filed: Feb. 26, 1991

Related U.S. Application Data

[63] Continuation-in-part of Ser. No. 631,576, Dec. 21, 1990, abandoned, which is a continuation of Ser. No. 402,947, Sep. 5, 1989, abandoned, which is a continuation-in-part of Ser. No. 348,548, May 8, 1989, abandoned, which is a continuation-in-part of Ser. No. 257,475, Oct. 13, 1988, abandoned.

[51] Int. Cl.$^5$ .................. C07C 221/00; C07C 225/00
[52] U.S. Cl. .................. 564/502; 548/494; 548/502
[58] Field of Search ........................ 564/502

[56] References Cited

U.S. PATENT DOCUMENTS 4,739,073  4/1988  Kathawala .................. 548/406

FOREIGN PATENT DOCUMENTS 90045    5/1959  Czechoslovakia .
363934   4/1990  European Pat. Off. .
945536   1/1964  United Kingdom .

OTHER PUBLICATIONS

Eilingsfeld et al., Angew. Chem. 72, 836–845 (1960).

*Primary Examiner*—David B. Springer
*Attorney, Agent, or Firm*—Gerald D. Sharkin; Richard E. Vila; Melvyn M. Kassenoff

[57] ABSTRACT

Process for the synthesis of compounds of the formula

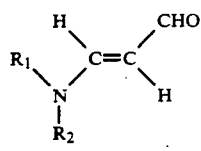

comprising the steps of (i) reacting a compound of the formula

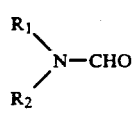

with oxalyl chloride or oxalyl bromide to form the corresponding compound of the formula

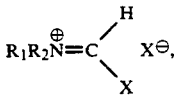

(ii) reacting said compound of the formula

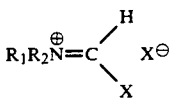

with a compound of the formula

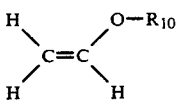

to form the corresponding compound of the formula

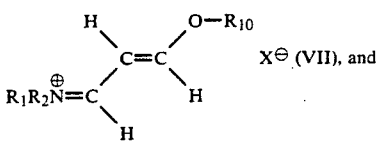

(iii) hydrolyzing said compound of the formula

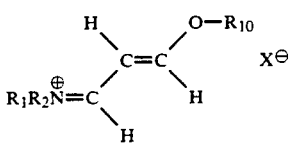

to obtain the corresponding compound of the formula

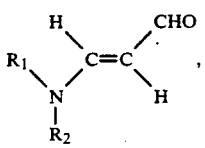

the use of the compounds of the formula

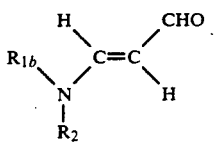

for the synthesis of the compounds of the formula (Abstract continued on next page.)

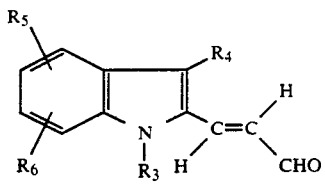 (II)

and the use of the intermediates of Formula VII for the direct synthesis of the compounds of Formula II, wherein R$_1$ is C$_{1-3}$alkyl, phenyl or phenyl substituted by 1 to 3 substituents each of which is independently C$_{1-3}$alkyl, C$_{1-3}$alkoxy, fluoro, chloro, bromo or nitro (maximum of two nitro groups), R$_{1b}$ is phenyl or phenyl substituted by 1 to 3 substituents each of which is independently C$_{1-3}$alkyl, C$_{1-3}$alkoxy, fluoro, chloro, bromo or nitro (maximum of two nitro groups), R$_2$ is C$_{1-3}$alkyl, one of R$_3$ and R$_4$ is

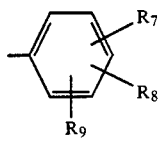

and the other is primary or secondary C$_{1-6}$alkyl not containing an asymmetric carbon atom, C$_{3-6}$cycloalkyl or phenyl-(CH$_2$)$_m$—, wherein R$_7$ is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy, R$_8$ is hydrogen, C$_{1-3}$alkyl, C$_{1-3}$alkoxy, trifluoromethyl, fluoro, chloro, phenoxy or benzyloxy, R$_9$ is hydrogen, C$_{1-2}$alkyl, C$_{1-2}$alkoxy, fluoro or chloro, and m is 1, 2 or 3, with the provisos that not more than one of R$_7$ and R$_8$ is trifluoromethyl, not more than one of R$_7$ and R$_8$ is phenoxy, and not more than one of R$_7$ and R$_8$ is benzyloxy, R$_5$ is hydrogen, C$_{1-3}$alkyl, n-butyl, i-butyl, t-butyl, C$_{3-6}$cycloalkyl, C$_{1-3}$alkoxy, n-butoxy, i-butoxy, trifluoromethyl, fluoro, chloro, phenoxy or benzyloxy, and R$_6$ is hydrogen, C$_{1-3}$alkyl, C$_{1-3}$alkoxy, trifluoromethyl, fluoro, chloro, phenoxy, or benzyloxy, with the provisos that not more than one of R$_5$ and R$_6$ is trifluoromethyl, not more than one of R$_5$ and R$_6$ is phenoxy, and not more than one of R$_5$ and R$_6$ is benzyloxy, R$_{10}$ is C$_{1-6}$alkyl, each X is chloro or bromo, and each X$^\ominus$ is chloride or bromide.

23 Claims, No Drawings

PROCESSES FOR THE SYNTHESIS OF 3-DISUBSTITUTED AMINOACROLEINS

This is a continuation-in-part of application Ser. No. 07/631,576, filed Dec. 21, 1990 and now, abandoned, which is a continuation of application Ser. No. 07/402,947, filed Sept. 5, 1989 and now abandoned, which is a continuation-in-part of application Ser. No. 07/348,548, filed May 8, 1989 and now abandoned, and a continuation-in-part of application Ser. No. 07/257,475, filed Oct. 13, 1988 and now abandoned, said application Ser. No. 07/348,548 also being a continuation-in-part of said application Ser. No. 07/257,475.

This invention relates to a process for the synthesis of compounds of the formula

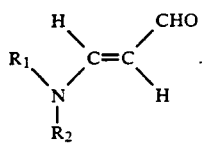

(I)

and to the use of certain such compounds for synthesizing compounds of the formula

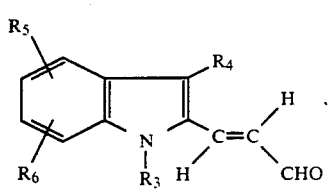

(II)

wherein $R_1$ is $C_{1-3}$alkyl, phenyl or phenyl substituted by 1 to 3 substituents each of which is independently $C_{1-3}$alkyl, $C_{1-3}$alkoxy, fluoro, chloro, bromo or nitro (maximum of two nitro groups), $R_2$ is $C_{1-3}$alkyl, one of $R_3$ and $R_4$ is

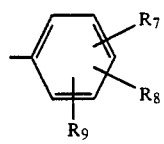

and the other is primary or secondary $C_{1-6}$alkyl not containing an asymmetric carbon atom, $C_{3-6}$cycloalkyl or phenyl—$(CH_2)_m$—, wherein $R_7$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_8$ is hydrogen, $C_{1-3}$alkyl, $C_{1-3}$alkoxy, trifluoromethyl, fluoro, chloro, phenoxy or benzyloxy, $R_9$ is hydrogen, $C_{1-2}$alkyl, $C_{1-2}$alkoxy, fluoro or chloro, and m is 1, 2 or 3, with the provisos that not more than one of $R_7$ and $R_8$ is trifluoromethyl, not more than one of $R_7$ and $R_8$ is phenoxy, and not more than one of $R_7$ and $R_8$ is benzyloxy, $R_5$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy, and $R_6$ is hydrogen, $C_{1-3}$alkyl, $C_{1-3}$alkoxy, trifluoromethyl, fluoro, chloro, phenoxy or benzyloxy, with the provisos that not more than one of $R_5$ and $R_6$ is trifluoromethyl, not more than one of $R_5$ and $R_6$ is phenoxy, and not more than one of $R_5$ and $R_6$ is benzyloxy.

This invention also relates to the use of intermediates in the synthesis of the compounds of Formula I, viz., the compounds of the formula

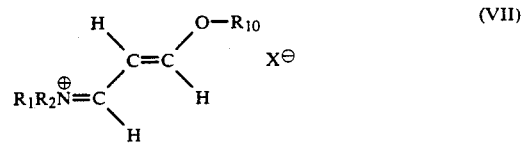

(VII)

for the direct synthesis of the compounds of Formula II.

The process for the synthesis of the compounds of Formula I (hereinafter Process A) comprises the steps of (i) reacting a compound of the formula

(III)

with a compound of the formula

X—CO—CO—X (IV)

to form the corresponding compound of the formula

(V)

(ii) reacting said compound of the formula

(V)

with a compound of the formula

(VI)

to form the corresponding compound of the formula

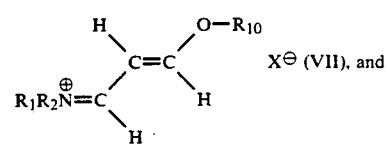

(VII), and (iii) hydrolyzing said compound of the formula

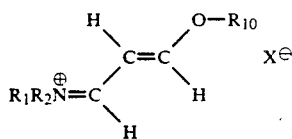

(VII)

to obtain the corresponding compound of the formula

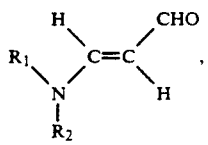

(I)

wherein $R_{10}$ is $C_{1-6}$alkyl, each X is chloro or bromo, each $X^\ominus$ is chloride or bromide, and $R_1$ and $R_2$ are as defined above.

Steps (i) and (ii) are preferably carried out in inert anhydrous organic media. These two steps may be carried out simultaneously of Step (ii) may follow Step (i); Step (iii) follows Step (ii) and, when employed, Step (iv), described below, follows Step (iii). The hydrolysis of Step (iii) is usually carried out with base, preferably aqueous base, but may be carried out with water and, when it is, the reaction mixture is subsequently treated with base (to neutralize the obtained acid addition salt).

$R_1$ is $R_{1a}$, where $R_{1a}$ is $C_{1-3}$alkyl, or $R_{1b}$, where $R_{1b}$ is phenyl or phenyl substituted by 1 to 3 substituents each of which is independently $C_{1-3}$alkyl, $C_{1-3}$alkoxy, fluoro, chloro, bromo or nitro (maximum of two nitro groups). $R_{1a}$ is preferably $C_{1-2}$alkyl and most preferably methyl. $R_{1b}$ is preferably $R'_{1b}$, where $R'_{1b}$ is phenyl or phenyl substituted by 1 or 2 substituents each of which is independently $C_{1-3}$alkyl, $C_{1-2}$alkoxy or chloro, more preferably $R''_{1b}$, where $R''_{1b}$ is phenyl or phenyl substituted by 1 or 2 methyl groups, and most preferably phenyl.

$R_2$ is preferably $C_{1-2}$alkyl and most preferably methyl.

$R_{10}$ is preerably $R_{10a}$, where $R_{10a}$ is primary or secondary $C_{2-4}$alkyl, more preferably $R_{10b}$, where $R_{10b}$ is n-$C_{2-4}$alkyl and even more preferably ethyl or n-butyl.

Each X is preferably chloro.

Each $X^\ominus$ is preferably chloride.

The base utilized in Step (iii) is preferably an inorganic base such as sodium carbonate, potassium carbonate, sodium hydroxide or potassium hydroxide and more preferably is sodium carbonate or potassium carbonate.

Preferred reaction conditions for Process A are as follows:

Step (i) (when carried out prior to Step (ii))

Temperature: $-20°-50°$ C.
Time: 1.5-5 hours
Reaction Medium: Liquid halogenated lower alkane, e.g., 1,2-dichloroethane and methylene chloride, or acetonitrile, methylene chloride and acetonitrile being most preferred
Molar Ratio of Reactants: 1-1.5 moles IV per mole III Step (ii) (when carried out subsequent to Step (i))

Temperature: $10°-60°$ C., $10°-40°$ C. being more preferred
Time: 0.5-3 hours

Reaction Medium: Same as Step (i)
Molar Ratio of Reactants: 1-1.5 moles VI per mole III utilized in Step (i)

Steps (i) and (ii) (when carried out simultaneously)

Temperature: $-15°-35°$ C.
Time: 2-6 hours
Reaction Medium: Same as Step (i) when carried out prior to Step (ii)
Molar Ratio of Reactants: 1-1.5 moles IV and 1-1.5 moles VI per mole III Step (iii)

Temperature: $0°-65°$ C.
Time: 0.5-3 hours
Reaction Medium: Water or mixture of water and reaction medium utilized in Step (ii)
Molar Ratio of Reactants: 2-4 equivalents base per mole IV utilized in Step (i)

Process A may be divided into two subprocesses depending upon the significance of $R_1$: (1) $R_1$ is $R_{1a}$ (Subprocess Aa) and (2) $R_1$ is $R_{1b}$ (Subprocess Ab).

The product of Step (iii) of Subprocess Aa often contains an appreciable amount of the compound of the formula

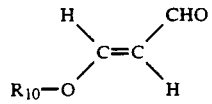

(VIII)

corresponding to the obtained compound of Formula I, the molar ratio of the compound of Formula I to the compound of Formula VIII typically being about 2:1. While it is, of course, possible to separate the compound of Formula I from that of Formula VIII by conventional means of separation such as those set forth below, it is preferable to subject the product of Step (iii), i.e., the crude compound of Formula I (a mixture of the compound of Formula I with the corresponding compound of Formula VIII), to Step (iv), viz.: (iv) treating the crude compound of the formula

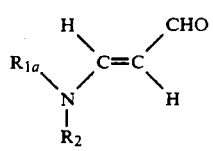

(IX)

with the corresponding compound of the formula

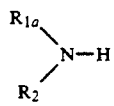

(X)

to convert any compound of the formula

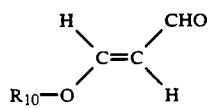

(VIII)

present therein into additional compound of the formula

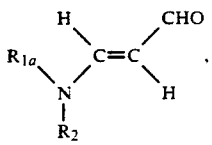

wherein $R_{1a}$, $R_2$ and $R_{10}$ are as defined above

The product of Step (iii) of Subprocess Ab may be subjected to an analogous Step (iv). However, there is usually no reason to do so since the product usually contains little or no compound of Formula VIII.

Preferred reactants in Subprocess Aa are those (a) wherein $R_1$ ($R_{1a}$) is $C_{1-2}$alkyl, $R_2$ is $C_{1-2}$alkyl, $R_{10}$ is $R_{10a}$, each X is chloro, and each $X^\ominus$ is chloride, (b) of (a) wherein $R_{10}$ is $R_{10b}$, (c) of (b) wherein $R_1$ ($R_{1a}$) is methyl, $R_2$ is methyl, and $R_{10}$ is ethyl, (d)–(f) of (a)–(c) wherein the base utilized in Step (iii) is sodium carbonate or potassium carbonate, and (g)–(i) of (d)–(f) wherein the base utilized in Step (iii) is potassium carbonate.

Preferred reaction conditions for Subprocess Aa, particularly when the reactants are those of Subgroups (a)–(i), more particularly when they are those of Subgroups (b), (c), (f), (h) and (i) and especially when they are those of Subgroups (c), (f) and (i), are:

Step (i)

Temperature: 0°–20° C., 0°–15° C. being more preferred and 5°–15° C. being even more preferred
Time: 1.5–4 hours
Reaction Medium: Liquid halogenated lower alkane, methylene chloride being most preferred
Molar Ratio of Reactants: 1–1.2 moles IV per mole III, 1.1–1.2 moles IV per mole III being more preferred Step (ii)

Temperature: 25°–40° C.
Time: 0.7–2.5 hours
Reaction Medium: Same as Step (i)
Molar Ratio of Reactants: 1–1.2 moles VI per mole III utilized in Step (i), 1.1–1.2 moles VI per mole III being more preferred Step (iii)

Temperature: 20°–65° C.
Time: 0.75–2 hours
Reaction Medium: Aqueous
Molar Ratio of Reactants: 2–4 equivalents base per mole IV utilized in Step (i)

Step (iv)

Temperature: 0°–20° C., 10°–20° C. being more preferred
Time 0.3–1 hour
Reaction Medium: $C_{1-4}$alkanol, methanol being most preferred
Molar Ratio of Reactants: 0.15–1 mole X per mole III utilized in Step (i), 0.15–0.4 mole X per mole III being more preferred.

In Subprocess Aa, Step (ii) is preferably carried out after Step (i).

Preferably, Subprocess Aa comprises the steps of (i) reacting N,N-dimethylformamide with oxalyl chloride in methylene chloride at a temperature of 0°–15° C. to form the compound of the formula

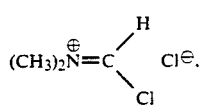

(ii) reacting said compound of the formula

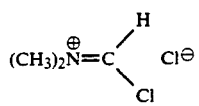

with ethyl vinyl ether in methylene chloride at a temperature of 25°–40° C. to form the compound of the formula

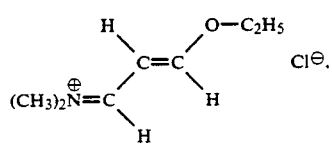

(iii) hydrolyzing said compound of the formula

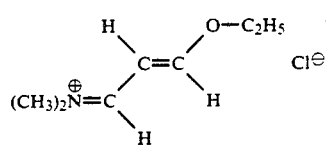

with water at 20°–60° C. and subsequently treating with potassium carbonate in an aqueous medium at a temperature of 20°–30° C. to form a mixture of the compounds of the formulae

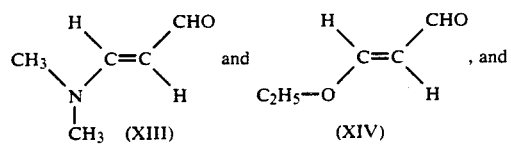

(iv) treating the mixture of the compounds of the formulae

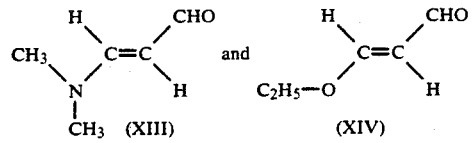

with dimethylamine in methanol at a temperature of 10°–20° C. to convert the compound of the formula

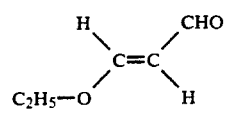

into additional compound of the formula

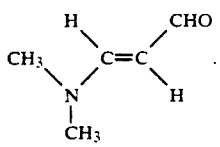

More preferably, in Subprocess Aa (1) the molar ratio of oxalyl chloride to N,N-dimethylformamide in Step (i) is 1–1.2:1, and Step (i) is carried out by adding oxalyl chloride to a solution of N,N-dimethylformamide in methylene chloride over a period of 1.5–4 hours at a rate such that the temperature is maintained at 5°–15° C., (2) in Step (ii) the molar ratio of ethyl vinyl ether to the N,N-dimethylformamide utilized in Step (i) is 1–1.2:1, and Step (ii) is carried out by adding ethyl vinyl ether to the reaction mixture over a period of 0.4–1.5 hours at a rate such that the temperature does not exceed 30° C. and, upon completion of the addition, refluxing the reaction mixture at 35°–40° C. for 0.3–1 hour and recovering as much methylene chloride as possible at a temperature not in excess of 45° C., (3) in Step (iii) the molar ratio of potassium carbonate to the oxalyl chloride utilized in Step (i) is 1–2:1, and Step (iii) is carried out by adding water to the product of Step (ii) stirred at 20°–30° C., allowing the temperature to rise to 45°–60° C., maintaining this temperature during the balance of the addition of the water and for an additional 0.3–1 hour, cooling the reaction mixture to 15°–25° C., adding an aqueous solution of potassium carbonate over a period of 0.3–1.25 hours at this temperature, extracting the mixture with methylene chloride and distilling as much methylene chloride as possible at a temperature not in excess of 45° C., and (4) in Step (iv) the molar ratio of dimethylamine to the N,N-dimethylformamide utilized in Step (i) is 0.15–0.4:1, and Step (iv) is carried out by adding anhydrous dimethylamine to a solution of the product of Step (iii) in methanol stirred at 10°–20° C. at a rate such that the temperature does not exceed 20° C. and distilling the solvent and any excess dimethylamine at a temperature not in excess of 120° C.

Preferred reactants in Subprocess Ab are those
(a) wherein $R_1$ ($R_{1b}$) is $R'_{1b}$, $R_2$ is $C_{1-2}$alkyl, $R_{10}$ is $R_{10a}$, each X is chloro, and each $X^{\ominus}$ is chloride,
(b) of (a) wherein $R_1$ ($R_{1b}$) is $R''_{1b}$, and $R_{10}$ is $R_{10b}$,
(c) of (b) wherein $R_1$ ($R_{1b}$) is phenyl, $R_2$ is methyl, and $R_{10}$ is ethyl or n-butyl, especially n-butyl,
(d)–(f) of (a)–(c) wherein the base utilized in Step (iii) is sodium carbonate or potassium carbonate, and
(g)–(i) of (d)–(f) wherein the base utilized in Step (iii) is sodium carbonate.

Preferred reaction conditions for Subprocess Ab, particularly when the reactants are those of Subgroups (a)–(i), more particularly when they are those of Subgroups (b), (c), (e), (f), (h) and (i) and especially when they are those of Subgroups (c), (f) and (i), are:

Step (i) (when carried out prior to Step (ii))
Temperature: −20°–45° C.
Time: 1.5–5 hours
Reaction Medium: Liquid halogenated lower alkane or acetonitrile, methylene chloride and acetonitrile being more preferred and acetonitrile being most preferred
Molar Ratio of Reactants: 1–1.2 moles IV per mole III, 1.1–1.2 moles IV per mole III being more preferred Step (ii) (when carried out subsequent to Step (i))
Temperature: 10°–40° C.
Time: 0.5–3 hours
Reaction Medium: Same as Step (i)
Molar Ratio of Reactants: 1–1.3 moles VI per mole III utilized in Step (i), 1.1–1.25 moles VI per mole III being more preferred Steps (i) and (ii) (when carried out simultaneously)
Temperature: −15°–35° C.
Time: 2–6 hours
Reaction Medium: Same as Step (i) when carried out prior to Step (ii)
Molar Ratio of Reactants: 1–1.5 moles IV and 1–1.5 moles VI per mole III Step (iii)
Temperature: 0°–35° C., 0°–30° C. being more preferred
Time: 0 5–1.5 hours
Reaction Medium: Mixture of water and reaction medium of Step (ii)
Molar Ratio of Reactants: 2–4 equivalents base per mole IV utilized in Step (i)

There are three preferred variants of Subprocess Ab, Variants Ab1, Ab2 and Ab3. In Variant Ab1 $R_{10}$ is ethyl and the reaction medium for Steps (i) and (ii) is methylene chloride, and in Variants Ab2 and Ab3 $R_{10}$ is n-butyl and the reaction medium for Steps (i) and (ii) is acetonitrile. In Variants Ab1 and Ab2, Step (ii) is carried out after Step (i) and in Variant Ab3 Steps (i) and (ii) are carried out simultaneously; in each variant Step (iii) follows Steps (i) and (ii).

Variant Ab1 of Subprocess Ab preferably comprises the steps of (i) reacting N-methylformanilide with oxalyl chloride in methylene chloride at a temperature of 15°–45° C. to form the compound of the formula

(ii) reacting said compound of the formula

with ethyl vinyl ether in methylene chloride at a temperature of 15°–40° C. to form the compound of the formula

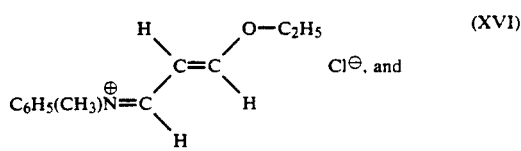

(iii) hydrolyzing said compound of the formula

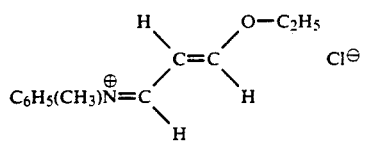 (XVI)

with sodium carbonate in a mixture of methylene chloride and water at a temperature of 20°-30° C. to obtain the compound of the formula

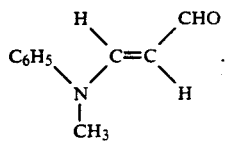 (XVII)

More preferably, in Variant Ab1 of Subprocess Ab, (1) the molar ratio of oxalyl chloride to N-methylformanilide in Step (i) is 1-1.2:1, and Step (i) is carried out by adding oxalyl chloride to a solution of N-methylformanilide in methylene chloride to a solution of N-methylformanilide in methylene chloride at 15°-20° C. over a period of 1-2 hours and, upon completion of the addition, gradually raising the temperature of the reaction mixture to 40°-45° C. over a period of 0.75-1.25 hours and then refluxing it for 0.75-1.25 hours, (2) in Step (ii) the molar ratio of ethyl vinyl ether to the N-methylformanilide utilized in Step (i) is 1-1.3:1, and Step (ii) is carried out by cooling the product of Step (i) to 15°-20° C., adding ethyl vinyl ether over a period of 0.5-1.5 hours at a rate such that the temperature does not exceed 30° C., and, upon completion of the addition, refluxing the reaction mixture for 0.3-0.7 hour, and (3) in Step (iii) the molar ratio of sodium carbonate to the oxalyl chloride utilized in Step (i) is 1-1.2:1, and Step (iii) is carried out by cooling the product of Step (ii) to 15°-20° C., adding, over a period of 0.5-1 hour, an aqueous solution of sodium carbonate at a rate such that the temperature of the reaction mixture is 20°-30° C. and, upon completion of the addition, stirring the mixture at 20°-30° C. for 0.2-0.5 hour, allowing the mixture to separate into two phases, separating the two phases and recovering the product from the organic phase.

Variant Ab2 of Subprocess Ab preferably comprises the steps of (i) reacting N-methylformanilide with oxalyl chloride in acetonitrile at a temperature of −20°-20° C. to form the compound of the formula

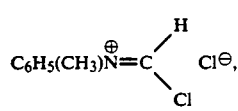 (XV)

(ii) reacting said compound of the formula

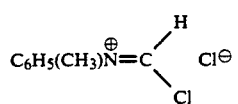 (XV)

with n-butyl vinyl ether in acetonitrile at a temperature of 10°-40° C. to form the compound of the formula

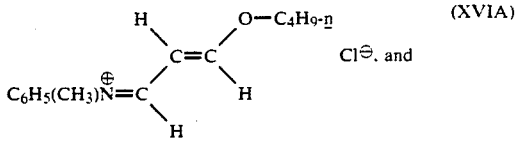 (XVIA)

(iii) hydrolyzing said compound of the formula

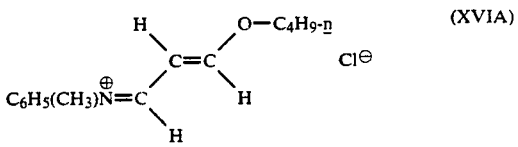 (XVIA)

with sodium carbonate in a mixture of acetonitrile and water at a temperature of 0°-25° C. to obtain the compound of the formula

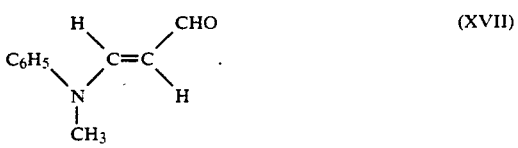 (XVII)

More preferably, in Variant Ab2 of Subprocess Ab, (1) the molar ratio of oxalyl chloride to N-methylformanilide in Step (i) is 1-1.2:1, and Step (i) is carried out by adding oxalyl chloride to a solution of N-methylformanilide in acetonitrile at −18°-8° C. over a period of 1-2 hours and, upon completion of the addition, gradually raising the temperature of the reaction mixture to 12°-20° C. over a period of 0.4-0.75 and then stirring it for 0.2-0.4 hour at this temperature, (2) in Step (ii) the molar ratio of n-butyl vinyl ether to the N-methylformanilide utilized in Step (i) is 1-1.2:1, and Step (ii) is carried out by adding n-butyl vinyl ether to the product of Step (i) stirred at 12°-20° C. over a period of 0.5-1.5 hours at a rate such that the temperature does not exceed 30° C., and, upon completion of the addition, stirring the reaction mixture for 0.3-0.7 hour at 25°-35° C., and (3) in Step (iii) the molar ratio of sodium carbonate to the oxalyl chloride utilized in Step (i) is 1-1.3:1, and Step (iii) is carried out by cooling the product of Step (ii) to 0°-5° C., adding, over a period of 0.5-1.2 hours, an aqueous solution of sodium carbonate at a rate such that the temperature of the reaction mixture is 5°-12° C. and, upon completion of the addition, adding toluene, stirring the mixture at 15°-25° C. for 0.2-0.5 hour, allowing the mixture to separate into two phases, separating the two phases and recovering the product from the organic phase.

Variant Ab3 of Subprocess Ab preferably comprises the steps of (i) and (ii) reacting N-methylformanilide with oxalyl chloride in acetonitrile at −10°-30° C. in the presence of n-butyl vinyl ether to form the compound of the formula

 (XV)

which compound then reacts with the n-butyl vinyl ether in the reaction mixture to form the compound of the formula

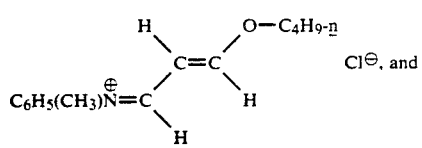 (XVIA)

(iii) hydrolyzing said compound of the formula

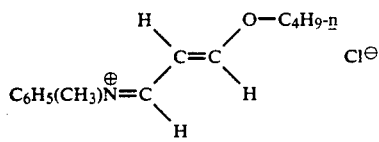 (XVIA)

with sodium carbonate in a mixture of acetonitrile and water at a temperature of 0°–25° C. to obtain the compound of the formula

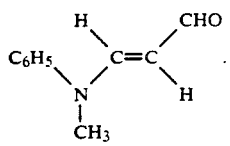 (XVII)

More preferably, in Variant Ab3 of Subprocess Ab, (1) in Steps (i) and (ii), the molar ratio of oxalyl chloride and n-butyl vinyl ether to N-methylformanilide is 1–1.2-:1–1.2:1, and Steps (i) and (ii) are carried out by adding a solution of N-methylformanilide and n-butyl vinyl ether in acetonitrile to a solution of oxalyl chloride in acetonitrile stirred at −10°–10° C. over a period of 2–3 hours and, upon completion of the addition, gradually raising the temperature of the reaction mixture to 20°–30° C. over a period of 0.4–1.5 hours and then stirring the reaction mixture at this temperature for 0.5–1.5 hours, and (2) in Step (iii), the molar ratio of sodium carbonate to the oxalyl chloride utilized in Step (i) is 1–1.3:1, and Step (iii) is carried out by cooling the product of Step (ii) to 0°–5° C., adding, over a period of 0.5–1.2 hours, an aqueous solution of sodium carbonate at a rate such that the temperature of the reaction mixture is 0°–12° C. and, upon completion of the addition, adding toluene, stirring the mixture at 15°–25° C. for 0.2–0.5 hour, allowing the mixture to separate into two phases, separating the two phases and recovering the product from the organic phase.

The process for the synthesis of the compounds of Formula II (hereinafter Process B) comprises the steps of (i) reacting a compound of the formula

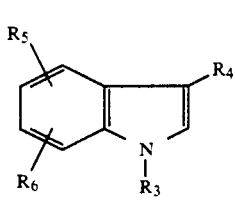 (XVIII)

with a compound of the formula

POX$_3$, X—CO—CO—X,
(XIX)    (IV)

X—CO—X or R$_{11}$—SO$_2$—X
(XX)           (XXI)

in an inert anhydrous organic medium to form the corresponding compound of the formula

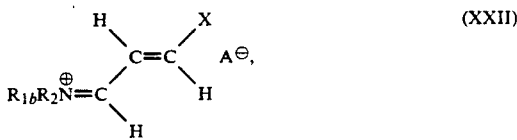 (XXII)

(ii) reacting said compound of the formula

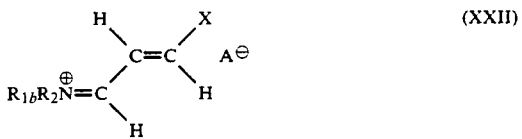 (XXII)

with a compound of the formula

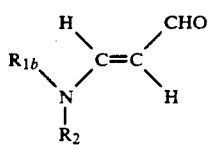 (XXIII)

in an inert anhydrous organic medium to form the corresponding compound of the formula

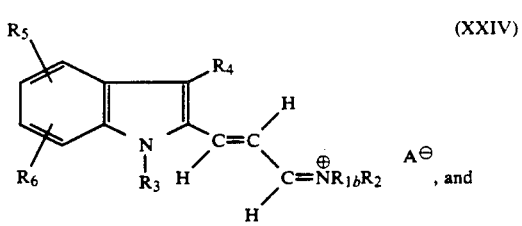 (XXIV), and (iii) hydrolyzing said compound of the formula

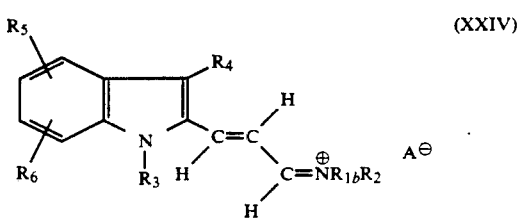 (XXIV)

to obtain the corresponding compound of the formula

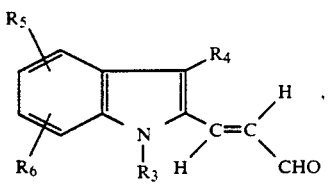 (II)

wherein $R_{11}$ is $C_{1-6}$alkyl, phenyl or 4-methylphenyl, $A^{\ominus}$ is $^{\ominus}PO_2X_2$ when a compound of Formula XIX is utilized in Step (i), $X^{\ominus}$ when a compound of Formula IV or XX is utlized in Step (i) and $R_{11}-SO_3^{\ominus}$ when a compound of Formula XXI is utilized in Step (i), and $R_{1b}$, $R_2-R_6$ and X are as defined above.

The preferences for $R_{1b}$, $R_2$ and X are set forth above, and the preferences for $R_3$, $R_4$, $R_5$ and $R_6$ are those set forth for $R_o$, R, $R_2$ and $R_3$, respectively, in U.S. Pat. No. 4,739,073. Said patent, particularly columns 3, 4, 6 and 7 thereof, is hereby incorporated by reference.

$R_{11}$ is preferably $R_{11a}$, where $R_{11a}$ is $C_{1-2}$ alkyl, phenyl or 4-methylphenyl, and most preferably methyl or 4-methylphenyl.

$A^{\ominus}$ is preferably $^{\ominus}PO_2X_2$ (since it is preferred to use a compound of Formula XIX in Step (i)) and most preferably $^{\ominus}PO_2Cl_2$ (since it is most preferred to use phosphorus oxychloride in Step (i)).

Preferred reactants (and final products) are (a)-(d) those wherein $R_{1b}$ is $R'_{1b}$, $R_2$ is $C_{1-2}$alkyl, each X is chloro, $A^{\ominus}$ is $^{\ominus}PO_2Cl_2$ (i.e., $POCl_3$ is is utilized in Step (i)), and $R_3-R_6$ have the significances of the corresponding variables of Groups (i), (ii), (xxi) and (xxii) of said U.S. Pat. No. 4,739,073, (e)-(h) those of (a)-(d) wherein $R_{1b}$ is $R''_{1b}$, and $R_3-R_6$ have the significances of the corresponding variables of Groups (v), (vi), (xxv) and (xxvi) of said U.S. Pat. No. 4,739,073, (i) and (j) those of (e) and (f) wherein $R_3$ is $C_{1-3}$alkyl, $R_4$ is phenyl, methylphenyl, fluorophenyl, dimethylphenyl or methyl-fluorophenyl, $R_5$ is hydrogen, $C_{1-3}$alkyl or 4- or 6-benzyloxy, and $R_6$ is hydrogen or methyl, (k) and (l) those of (g) and (h) wherein $R_3$ is phenyl, methylphenyl, fluorophenyl, dimethylphenyl or methyl-fluorophenyl, $R_4$ is $C_{1-3}$alkyl, $R_5$ is hydrogen, $C_{1-3}$alkyl or 4- or 6-benzyloxy, and $R_6$ is hydrogen or methyl, (m)-(p) those of (i)-(1) wherein $R_5$ is hydrogen, and $R_6$ is hydrogen, (q)-(t) those of (m)-(p) wherein $R_{1b}$ is phenyl, and $R_2$ is methyl, (u) that of (q) wherein $R_3$ is 1-methylethyl, and $R_4$ is 4-fluorophenyl, and (v) that of (s) wherein $R_3$ is 4-fluorophenyl, and $R_4$ is 1-methylethyl.

The preferred bases for Step (iii) are inorganic hydroxides such as sodium hydroxide and potassium hydroxide, especially the former. However, as set forth infra, it is most preferred not to employ any base in Step (iii).

Preferred reaction conditions for Process B are:

Step (i)

Temperature: $-10°-25°$ C., $-10°-10°$ C. being more preferred
Time: 0.1-1.2 hours, 0.5-1 hour being more preferred
Reaction Medium: Lower alkyl nitrile, acetonitrile being most preferred
Molar Ratio of Reactants: 1-1.5 moles XIX, IV, XX or XXI, preferably XIX, per mole XVIII, 1.1-1.3 moles XIX per mole XVIII being more preferred Step (ii)

Temperature: 60°-100° C., 65°-85° C. being more prefered
Time: 2-30 hours, 3-24 hours being more preferred
Reaction Medium: Same as Step (i)
Molar Ratio of Reactants: 1-5 moles XXII per mole XXIII, 2-3 moles XXII per mole XXIII being more preferred (100% yield in Step (i) assumed in each case)

Step (iii)

Temperature: 10°-40° C. when base is employed and 35°-60° C. when it is not
Time: 0.1-1 hour when base is employed and 2-4 hours when it is not
Solvent: Mixture of water and reaction medium of Step (ii)
Molar Ratio of Reactants: When base is employed, 4-8 equivalents base, preferably sodium hydroxide or potassium hydroxide, per mole XIX, IV, XX or XXI utilized in Step (i)

Even more preferred reaction conditions for Process B, particularly when the reactants and final products are those of Subgroups (a)-(v), more particularly when they are those of Subgroups (b)-(v), even more particularly when they are those of Subgroups (i)-(v), especially when they are those of Subgroups (i), (j), (m), (n), (q), (r) and (u) and most especially when they are those of Subgroup (u), are:

Step (i)

Temperature: $-10°-10°$ C.
Time: 0.75-1 hour
Reaction Medium: Acetonitrile
Molar Ratio of Reactants: 1.1-1.3 moles XIX per mole XVIII Step (ii)

Temperature: 65°-85° C., 80°-83° C. being more preferred
Time: 3-16 hours, 3-10 hours being more preferred
Reaction Medium: Acetonitrile
Molar Ratio of Reactants: 2-3 moles XXII per mole XXIII, 2.1-2.5 moles XXII per mole XXIII being more preferred (100% yield in Step (i) assumed in each case)

Step (iii)

Temperature: 20°-35° C., 25°-35° C. being more preferred when base is employed and 35°-55° C. when it is not
Time: 0.3-0.7 hours when base is employed and 2-3 hours when it is not
Reaction Medium: Mixture of water and reaction medium of Step (ii)
Molar Ratio of Reactants: When base is employed, 4-6 equivalents base, preferably sodium hydroxide, per mole XIX utilized in Step (i)
It is most preferred not to employ base in Step (iii).

Processes A and B may be combined with the omission of Step (iii) of Process A and Step (i) of Process B, and, in the combined processes, all of the compounds of Formula VII, not just those wherein $R_1$ is $R_{1b}$, may be employed. In the combined process (hereinafter Process AB), the product of Step (ii) of Process A, i.e., the compound of Formula VII, is reacted with the compound of Formula XXIII. Process AB, therefore, comprises the steps of (i) reacting a compound of the formula

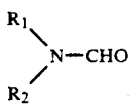   (III)

with a compound of the formula

X—CO—CO—X   (IV)

to form the corresponding compound of the formula

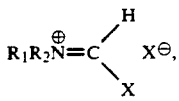   (V)

(ii) reacting said compound of the formula

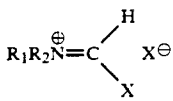   (V)

with a compound of the formula

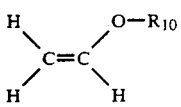   (VI)

to form the corresponding compound of the formula

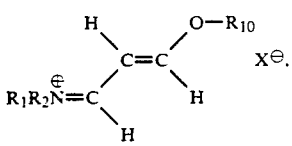   (VII)

(iii) reacting said compound of the formula

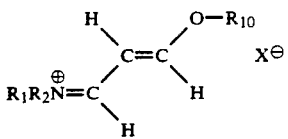   (VII)

with a compound of the formula

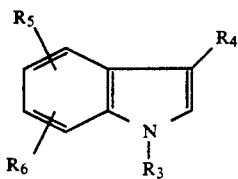   (XXIII)

in the presence of a scavenger for the compound of the formula $R_{10}$—OH that is formed in the reaction to form the corresponding compound of the formula

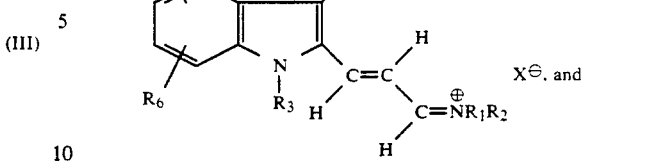   (XXV)

(iv) hydrolyzing said compound of the formula

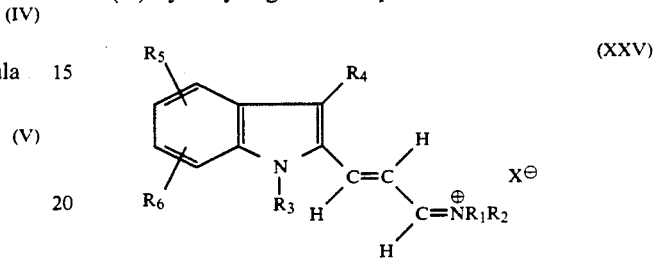   (XXV)

to obtain the corresponding compound of the formula

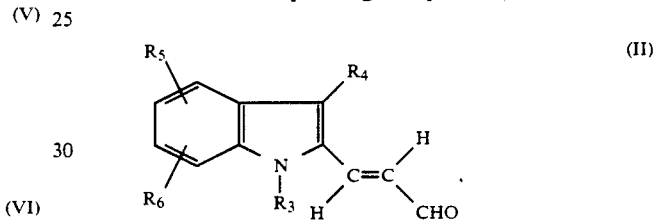   (II)

wherein $R_1$-$R_6$, $R_{10}$, X and X are as defined above.

Steps (i) and (ii) may be carried out simultaneously or Step (ii) may follow Step (i); Step (iii) follows Step (ii), and Step (iv) follows Step (iii). Steps (i)-(iii) are preferably carried out in inert anhydrous organic media. The scavenger for the compound of the formula $R_{10}$—OH that is formed in Step (iii) is preferably a compound of Formula XIX and, when each X is chloro, the compound of Formula XIX also serves as a solvent.

In Process AB, $R_1$ is preferably $R_{1b}$, more preferably $R'_{1b}$, even more preferably $R'_b$ and most preferably phenyl, and the preferences for $R_2$, $R_3$, $R_4$, $R_5$, $R_6$ and $R_{10}$ are as set forth above. $R_{10}$ is most preferably ethyl. When a compound of Formula XIX is utilized, it is preferably phosphorus oxychloride.

Preferred reactants and (final products) are (a)-(d) those wherein $R_{1b}$ is $R'_{1b}$, $R_2$ is $C_{1-2}$ alkyl, $R_{10}$ is $R_{10a}$, $R_3$-$R_6$ have the significances of the corresponding variables of Groups (i), (ii), (xxi) and (xxii) of said U.S. Pat. No. 4,739,073, and the scavenger is phosphorus oxychloride, (e)-(h) those of (a)-(d) wherein $R_{1b}$ is $R''_{1b}$, $R_{10}$ is $R_{10b}$, and $R_3$-$R_6$ have the significances of the corresponding variables of Groups (v), (vi), (xxv) and (xxvi) of said U.S. Pat. No. 4,739,073, (i) and (j) those of (e) and (f) wherein $R_3$ is $C_{1-3}$alkyl, $R_4$ is phenyl, methylphenyl, fluorophenyl, dimethylphenyl or methyl-fluorophenyl, $R_5$ is hydrogen, $C_{1-3}$alkyl or 4- or 6-benzyloxy, $R_6$ is hydrogen or methyl, and $R_{10}$ is ethyl, (k) and (l) those of (g) and (h) wherein $R_3$ is phenyl, methylphenyl, fluorophenyl, dimethylphenyl or methyl-fluorophenyl, $R_4$ is $C_{1-3}$alkyl, $R_5$ is hydrogen, $C_{1-3}$alkyl or 4- or 6-benzyloxy, $R_6$ is hydrogen or methyl, and $R_{10}$ is ethyl, (m)-(p) those of (i)-(l) wherein $R_5$ is hydrogen, and $R_6$ is hydrogen, (q)-(t) those of (m)-(p) wherein $R_{1b}$ is phenyl, and $R_2$ is methyl, (u) that of (q) wherein $R_3$ is 1-methylethyl, and $R_4$ is 4-fluorophenyl, and (v) that of (s) wherein $R_3$ is 4-fluorophenyl, and $R_4$ is 1-methylethyl.

Preferred reaction conditions for Process AB, particularly when the reactants and final products are those of Subgroups (a)-(v), more particularly when they are those of Subgroups (b)-(v), even more particularly when they are those of Subgroups (i)-(v), especially when they are those of Subgroups (i), (j), (m), (n), (q), (r) and (u) and most especially when they are those of Subgroup (u), are:

Step (i) (when carried out prior to Step (ii))

Temperature: $-20°-45°$ C.
Time: 1.5-5 hours
Reaction Medium: Phosphorus oxychloride, liquid halogenated lower alkane or acetonitrile, phosphorus oxychloride, methylene chloride and acetonitrile being more preferred and phosphorus oxychloride being most preferred
Molar Ratio of Reactants: 1-1.2 moles IV per mole III, 1.1-1.2 moles IV per mole III being more preferred Step (ii) (when carried out subsequent to Step (i))

Temperature: 10°-40° C.
Time 0.5-3 hours
Reaction Medium: Same as Step (i)
Molar Ratio of Reactants: 1-1.3 moles VI per mole III utilized in Step (i), 1.1-1.25 moles VI per mole III being more preferred Steps (i) and (i)) (when carried out simultaneously)

Temperature: $-15°-45°$ C. (preferably commence reaction at $-15°-0°$ C. and, after all reactants have been combined, gradually heat to 30°-45° C.)
Time: 2-6 hours
Reaction Medium Same as Step (i) when carried out prior to Step (ii)
Molar Ratio of Reactants: 1-1.3 moles IV and 1-1.3 moles VI per mole III (preferably molar amount of IV slightly exceeds that of VI)

Step (iii)

Temperature: 65°-100° C., 65°-95° C. being more prefered
Time: 3-30 hours, 3-10 hours being more preferred
Reaction Medium: Mixture of acetonitrile and phosphorus oxychloride
Molar Ratio of Reactants: 1-5 moles VII and 1-5 moles of a scavenger for the compound of the formula $R_{10}$—OH that is formed (preferably a compound of Formula XIX) per mole XXIII, 2-3 moles VII and 2-4 moles XIX per mole XXIII being more preferred (in each case, molar amount of the scavenger preferably exceeds molar amount of VII and 100% yield in Steps (i) and (ii) is assumed)

Step (iv)

Temperature: 10°-40° C. when base is employed and 35°-60° C. when it is not

Time: 0.1-1 hour when base is employed and 1.5-4 hours when it is not
Solvent: Mixture of water and reaction medium of Step (iii)
Molar Ratio of Reactants: When base is employed, 4-8 equivalents base, preferably sodium hydroxide or potassium hydroxide, per mole scavenger, e.g., compound of Formula XIX It is preferred to carry out Steps (i) and (ii) simultaneously and not to employ any added base in Step (iv).

More preferably, Steps (i) and (ii) of Process AB are carried out simultaneously by slowly adding a mixture of the compounds of Formulae IV and VI to a mixture of the compond of Formula IV and the solvent (preferably phosphorus oxychloride) stirred at $-b\ 15°-0°$ C. at a rate such that the temperature of the reaction mixture does not exceed 0° C. (preferably over a period of 1-2 hours), slowly warming the reaction mixture to 30°-45° C. (preferably over a period of 20-45 minutes) and stirring the reaction mixture at this temperature (preferably for an additional 20-60 minutes). 1.05-1.2 moles of the compound of Formula IV, 1.05-1.2 moles of the compound of Formula VI and, when phosphorus oxychloride is the solvent, 1.1-1.3 moles of it per mole of the compound of Formula III are preferably utilized, the molar amount of the compound of Formula IV more preferably exceeding that of the compound of Formula VI and the molar amount of phosphorus oxychloride, when used, exceeding that of the compound of Formula IV. At least most of the unreacted compounds of Formulae IV and VI are distilled at reduced pressure. Step (iii) is preferably carried out by adding the compound of Formula XXIII, acetonitrile and, if phosphouus oxychloride is not already present, the compound of Formula XIX to the product of Steps (i) and (ii) stirred at 30°-45° C., slowly heating the reaction mixture to reflux (preferably over a period of 20-60 minutes) and refluxing it for 4-6 hours; preferably, 0.3-0.5 mole of the compound of Formula XXIII and 1.05-1.2 moles of the compound of Formula XIX per mole of the compound of Formula III utilized in Step (i) are utilized. Step (iv) is preferably carried out by diluting the product of Step (iii) with acetonitrile and, at a temperature of 35°-50° C., slowly adding 0.5-4 l. of water per mole of the compound of Formula XXIII utilized in Step (iii) (preferably over a period of 10-45 minutes) and stirring the reaction mixture at 50°-60° C. for 1-3 hours. The compound of Formula II is preferably isolated from the reaction mixture as in Example 7.

Steps (i) and (ii) of Process A (including Subprocesses Aa and Ab and the variants thereof), Steps (i) and (ii) of Process B, Step (i)-(iii) of Process AB and, preferably, Step (iv) of Subprocess Aa are carried out under anhydrous conditions and an inert atmosphere, preferably dry helium, argon or nitrogen, or a mixture thereof, usually dry nitrogen. Step (iii) of Process A (including Subprocesses Aa and Ab and the variants thereof) and Process B and Step (iv) of Process AB are often, but need not be, carried out under an inert atmosphere.

Most of the molar amounts (ratios) given above are merely exemplary and may be varied, as is evident to one of ordinary skill in the art. For example, in a reaction of two compounds one of which is readily available and one of which is not, an excess of the readily available compound may be used to drive the reaction towards completion (unless the use of an excess would increase the synthesis of an undesired compound).

Likewise, most of the temperature ranges given above are merely exemplary, and it is within the ability of one of ordinary skill in the art to vary those that are not critical. All temperatures are internal temperatures, unless otherwise indicated.

As utilized above, the term "reaction medium" embraces mixtures of liquids and implies that the reaction medium is a liquid at the desired reaction temperature. It should, therefore, be understood that not all of the liquids listed for a particular step may be utilized for the entire recited temperature range. It should also be understood that the reaction medium must be at least substantially inert to the reactants employed, intermediates generated and end products under the reaction conditions utilized.

It should be understood that the reaction temperature may exceed the boiling point of a reactant or the reaction medium if a condenser or a closed system (reaction bomb) is utilized.

The reaction times set forth above are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding descriptions of Processes A, B and AB.

The product of each process may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Usually, however, the crude product of each process is sufficiently pure to be employed without purification.

Compounds of Formulae I, II and XXIII are known. See said U.S. Pat. No. 4,739,073 which discloses the compounds of Formula I wherein $R_1$ is $R_{1a}$, their use for the synthesis of the compounds of Formula II, the compounds of Formula XXIII and the use of the compounds of Formula II for the synthesis of indole analogs of mevalonolactone and derivatives thereof (the compounds of Formula I of said patent) which are useful as HMG-CoA reductase inhibitors. Since they inhibit cholesterol biosynthesis, they lower the blood cholesterol level and, therefore, are useful in the treatment of hypercholesterolemia, hyperlipoproteinemia and atherosclerosis. As set forth above, said patent is hereby incorporated by reference. Also incorporated by reference are application Ser. No. 06/722,288, filed Apr. 11, 1985 by Faizulla G. Kathawala, as a continuation-in-part of the application issuing as U.S. Pat. No. 4,739,073, which discloses, inter alia, improvements in the synthesis of the compounds Formula XXIII of this application and those of Formula I of said United States patent, and application Ser. No. 07/482,433, filed Feb. 20, 1990 as a continuation-in-part of application Ser. No. 07/355,531, filed May 22, 1989 by Prasad K. Kapa and Kau-Ming Chen, both of which disclose additional improvements in the synthesis of the compounds of Formula I of the aforementioned United States patent.

Compounds of Formula I and their synthesis are also disclosed in British Patent 945,536 and Czechoslovakian Patent 90,045. However, the processes disclosed therein differ from Process A with respect to, for example, the use of phosgene or phosphorus trichloride, pentachloride or oxychloride rather than oxalyl chloride or bromide.

Pages 4 and 10 and Claims 13-15 of greatgreatgrandparent application Ser. No. 07/257,475, pages 2-4, 7, 10, 11 and 14-18 and the claims of greatgrandparent application Ser. No. 07/348,548 and pages 1-19 and the claims of grandparent application Ser. No. 07/402,947 are hereby incorporated by reference as if set forth herein in their entirety.

The following examples constitute representative embodiments of the processes of this invention. However, it should be understood that they are for purposes of illustration only.

EXAMPLE 1

3-Dimethylaminoacrolein ((E)-3-dimethylaminoprop-2-enal)

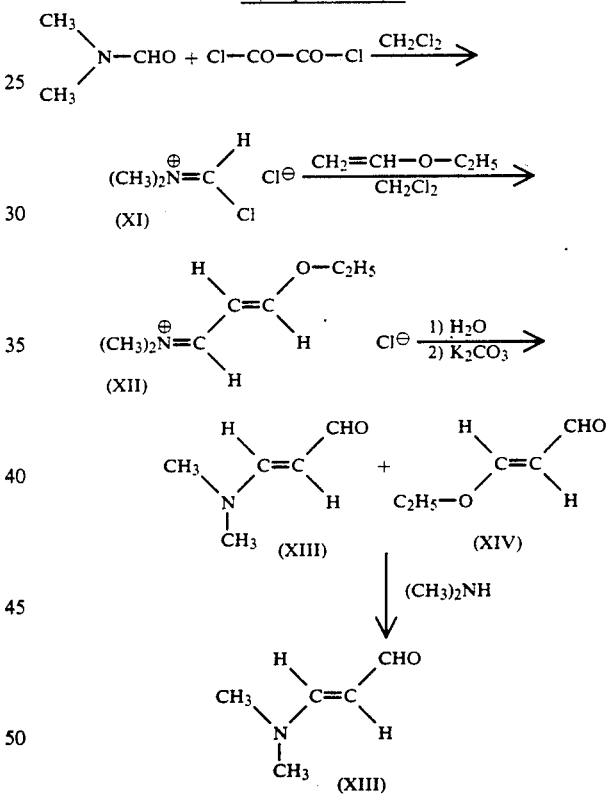

A 12 l. four-neck round bottom flask equipped with a stirrer, brine-filled condenser, thermometer, caustic scrubber, addition funnel and cooling bath is charged, under a blanket of nitrogen, with 4.0 l. of methylene chloride and 438 g. (5.99 moles) of N,N-dimethylformamide. The solution is cooled to 7° C., and 860 g. (6.8 moles) of oxalyl chloride is added over a period of 2.5 hours at a rate such that little or no solvent and/or reagent is swept into the condenser by the carbon dioxide and carbon monoxide that form, while maintaining the temperature of the reaction mixture at 5°-10° C. A white solid forms. 483 g. (6.7 moles) of ethyl vinyl ether is added over a period of 30-60 minutes while maintaining a maximum temperature of 25°-28° C., the addition being very exothermic. A brown-red solution results.

The reaction mixture is heated at 37°-38° C. for 30 minutes, refluxing taking place. As much methylene chloride as possible is recovered by distillation at 30-40 mm. Hg and 45° C., and, after the distillation ceases, the reaction mixture is maintained at 30 mm. Hg and 45° C. for 30 minutes to obtain a dark brown stirrable oil. The reaction mixture is cooled to 20° C., and 450 ml. of water is added over a period of ~30 minutes; the exotherm is allowed to raise the temperature to 60° C., and this temperature is maintained for the balance of the addition. The mixture is stirred at 50°-60° C. for 30 minutes and cooled to 20° C. A solution of 1.71 Kg. (12.35 moles) of anhydrous potassium carbonate in 3.6 l. of water is added over a period of 30-45 minutes while maintaining the temperature at 20°-22° C. The aqueous layer is extracted with 4 l. of methylene chloride, the bottom methylene chloride layer is separated, and the top aqueous layer is extracted four times with 1 l. portions of methylene chloride. The five methylene chloride phases are combined, dried over 500 g. of anhydrous sodium sulfate and filtered, and the solid is washed twice with 250 ml. portions of methylene chloride. The washings and filtrate are combined, and as much methylene chloride as possible is recovered by distillation at 20-40 mm. Hg and 45° C. to obtain a thick stirrable oil. The oil is cooled to 20° C., 500 ml. of methanol is added, the mixture is cooled to 10° C., and 60 g. (1.33 moles) of anhydrous dimethylamine is added while maintaining a maximum temperature of 20° C. As much solvent as possible is recovered by distillation at 20-30 mm. Hg and ~70° C., the pressure is lowered to 3-4 mm. Hg, and the distillation is continued while gradally raising the temperature until it reaches 120° C. and the vapor temperature reaches 115° C. to obtain the 89.7% pure product as an oil (412 g. (62%)). B.p. 271°-272.8° C.

EXAMPLE 2

3-N-methyl-N-phenylaminoacrolein
((E)-3-N-methyl-N-phenylaminoprop-2-enal)

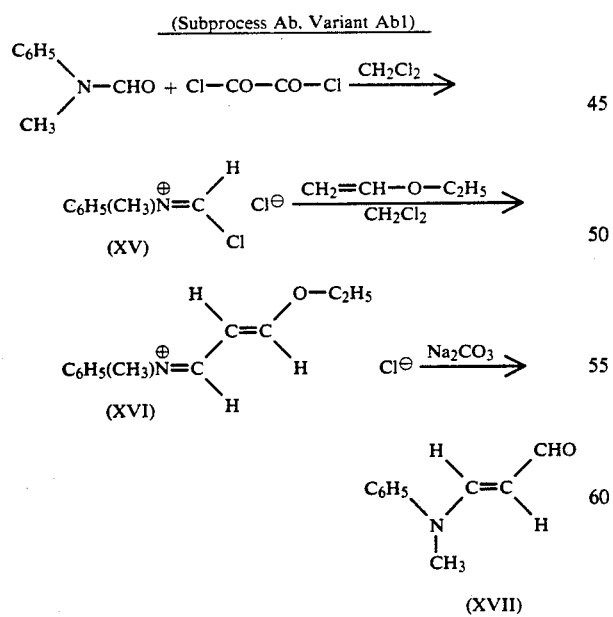

(Subprocess Ab. Variant Ab1)

A 12 l. four-neck round bottom flask equipped with a stirrer, brine-filled condenser, thermometer, caustic scrubber, addition funnel and cooling bath is charged, under a blanket of nitrogen, with 3.0 l. of methylene chloride and 1.02 kg. (7.4 moles) of N-methylformanilide. The solution is cooled to 15° C., and 1.10 kg. (8.67 moles) of oxalyl chloride is added over a period of 1.5 hours at a rate such that little or no solvent and/or reagent is swept into the bottom of the brine-filled condenser, while maintaining a temperature of 15°-17° C. under gentle refluxing. The reaction mixture is slowly warmed to 43° C. over a period of 1hour, refluxed for 1 hour at 43°-45° C. to obtain a clear yellow solution and cooled to 15° C. 648 g. (8.99 moles) of ethyl vinyl ether is added over a period of 40-60 minutes while maintaining a maximum temperature of 28°-29° C., the reaction being very exothermic. The resulting brown-red solution is heated at 38°-39° C. for 30 minutes, refluxing taking place, and is cooled to 15° C. A solution of 960 g. (9.05 moles) of anhydrous sodium carbonate in 4.5 l. of water is added over a period of 45-60 minutes while maintaining a temperature of 22°-30° C., the addition being very exothermic. The mixture is stirred at 22°-25° C. for 15 minutes and allowed to stand for 15 minutes to permit separation into two phases. The organic phase is separated, and the aqueous phase is extracted with 1.25 l. of methylene chloride. The methylene chloride extract is combined with the previous organic phase, and the combined solution is extracted with 1 l. of water. The aqueous extract is back extracted with 250 ml. of methylene chloride, and this methylene chloride extract is combined with the previous organic phase. As much methylene chloride as possible is recovered by distillation at 20-40 mm. Hg and 60° C., and the residual oil is heated at 20-30 mm. Hg and 60°-65° C. for 4 hours to obtain the 83.5% pure product as an oil (1.295 kg. (90.7%)). The oil may be crystallized by the procedure of Example 5 (m.p. 44°-45° C.) or from 1:1 isopropanol:n-hexane (m.p. 46°-47° C.). (Lit. 46°-47° C.)

EXAMPLE 3

3-N-methyl-N-phenylaminoacrolein
((E)-3-N-methyl-N-phenylaminoprop-2-enal)

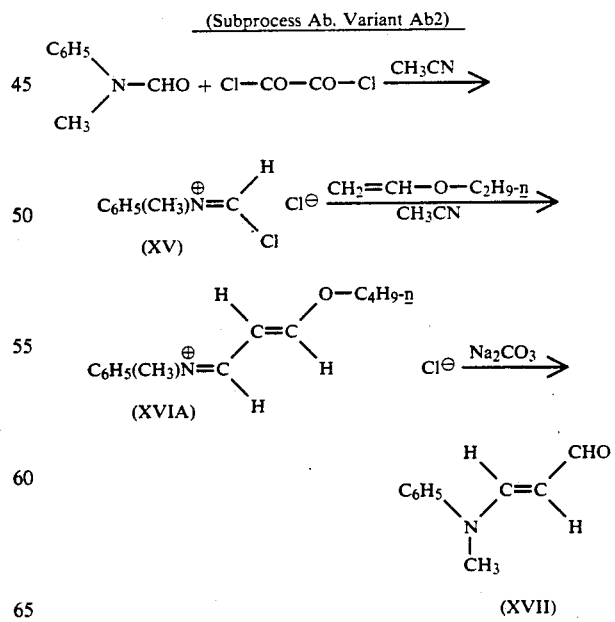

(Subprocess Ab. Variant Ab2)

A 5 l. four-neck round bottom flask equipped with a stirrer, brine-filled condenser, thermometer, caustic scrubber, addition funnel and cooling bath is charged, under a blanket of nitrogen, with 350 ml. of acetonitrile and 425 g. (3.8 moles) of N-methylformanilide. The solution is cooled to −15° C., and 440 g. (3.46 moles) of oxalyl chloride is added over a period of 1.5 hours at a rate such that little or no solvent and/or reagent is swept into the bottom of the brine-filled condenser (maintained at −25°-−20° C.), while maintaining a temperature of −15°-−10° C. under gentle refluxing. The reaction mixture is slowly warmed to 15° C. over a period of 30 minutes and stirred for 15 minutes at 15°-18° C. 339.5 g. (3.39 moles) of n-butyl vinyl ether is added over a period of 45 minutes while maintaining a maximum temperature of 28°-30° C., the reaction being very exothermic. The reaction mixture is stirred at 30°-35° C. for 30 minutes to obtain a red-brown solution and is cooled to 0° C. A solution of 395 g. (3.73 moles) of anhydrous sodium carbonate in 1.75 l. of water is added over a period of 40-60 minutes while maintaining a temperature of 8°-10° C., the addition being very exothermic. 1.75 l. of toluene is added, and the mixture is stirred at 20°-22° C. for 15 minutes and allowed to stand for 15 minutes to permit separation into two phases. The organic phase is separated and washed twice with 150 ml. portions of water. As much toluene as possible is recovered by distillation at 20-80 mm. Hg and 60°-90° C., and the residual oil is heated at 20-30 mm. Hg and 89°-90° C. for 30 minutes to obtain the 86.6% pure product as an oil (492 g. (85.7%))

If the reaction mixture is stirred at 28°-30° C. for 30 minutes instead of at 30°-35° C., a 90.7% yield of a 92.3% pure product is obtained.

The oil may be crystallized by the procedure of Example (m.p. 44°-45° C.) or from 1:1 isopropanol:n-hexane (46°-47° C.). (Lit. 46°-47° C.)

EXAMPLE 4

3-N-methyl-N-phenylaminoacrolein
((E)-3-N-methyl-N-phenyl-aminoprop-2-enal)

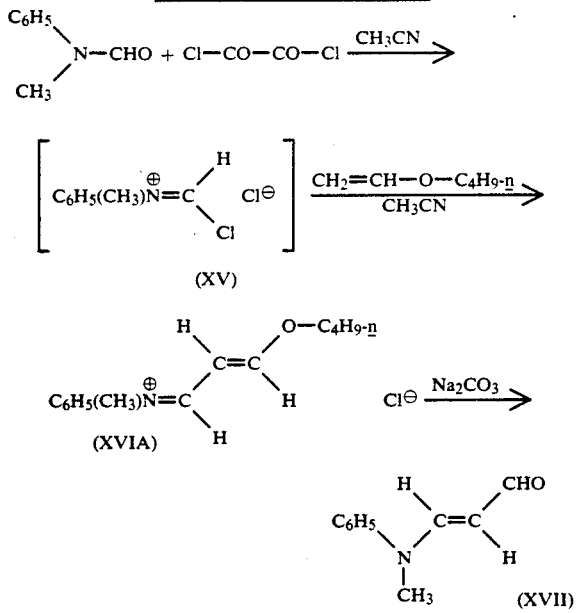

A 12 l. four-neck round bottom flask equipped with a stirrer, brine-filled condenser, thermometer, caustic scrubber, addition funnel and cooling bath is charged, under a blanket of nitrogen, with 1.056 kg. (8.15 moles) of oxalyl chloride and 480 ml. of acetonitrile. The solution is cooled to −10° C., and a mixture of 1.02 kg. (7.395 moles) of N-methylformanilide, 816 g. (7.98 moles) of n-butyl vinyl ether and 360 ml. of acetonitrile is added over a period of 2.5 hours at a rate such that little or no solvent and/or reagent is swept into the bottom of the brine-filled condenser (main at −25°-−20° C.), while maintaining a temperature of −10°-−5° C. under gentle refluxing. The resulting homogeneous orange reaction mixture is slowly warmed to 20° C. over a period of 30 minutes; a slight exotherm raises the temperature to 28° C. over a period of 30 minutes. The reaction mixture is stirred at 28°-30° C. for 1 hour to obtain a brown homogeneous mixture and is cooled to 0° C. A solution of 948 g. (8.94 moles) of anhydrous sodium carbonate in 4.20 l. of water is added over a period of 45-60 minutes while maintaining a temperature of 8°-10° C., the addition initially being very exothermic. 3.60 l. of toluene is added, and the mixture is stirred at 20°-22° C. for 15 minutes and allowed to stand for 15 minutes to permit separation into two phases. The organic phase is separated and washed twice with 360 ml. portions of water. As much toluene as possible is recovered by distillation at 20-80 mm. Hg and 60°-90° C., and the residual oil is heated at 20-30 mm. Hg and 89°-90° C. for 30 minutes to obtain the 89.1% pure product as an oil (1.16 kg. (86.6%)). B.p. 244° C. (dec.). The oil may be crystallized by the procedure of Example 5 (m.p. 44°-45° C.) or from 1:1 isopropanol:n-hexane (46°-47° C.). (Lit. 46°-47° C.)

EXAMPLE 5

3-N-methyl-N-phenylaminoacrolein
((E)-3-N-methyl-N-phenyl-aminoprop-2-enal)

815 ml. of n-hexane is added to a solution of 1.0 kg. of 88% pure 3-N-methyl-N-phenylaminoacrolein dissolved in 445 ml. of isopropanol at 45°-50° C., the mixture is cooled to 0° C. over a 30 minute period while being vigorously agitated, and 0.1 g. of 3-N-methyl-N-phenylaminoacrolein seed crystals is added at 0° C. The resulting slurry is cooled to −15° C. over a 30 minute period, maintained at −15°-−13° C. for an additional 30 minutes and quickly filtered at −15°-−10° C. The obtained solid is washed twice with 200 ml. portions of cold (−10° C.) 35:65 isopropanol:n-hexane and vacuum dried at 30°-35° C. to constant weight to obtain the 99% pure product as a light brown solid (723 g. (82.3%)), m.p. 44°-45° C.

EXAMPLE 6

(E)-3-[3'-(4''-fluorophenyl)-1'-(1''-methylethyl)-1H-indol-2'yl]prop-2-enal (Process B)

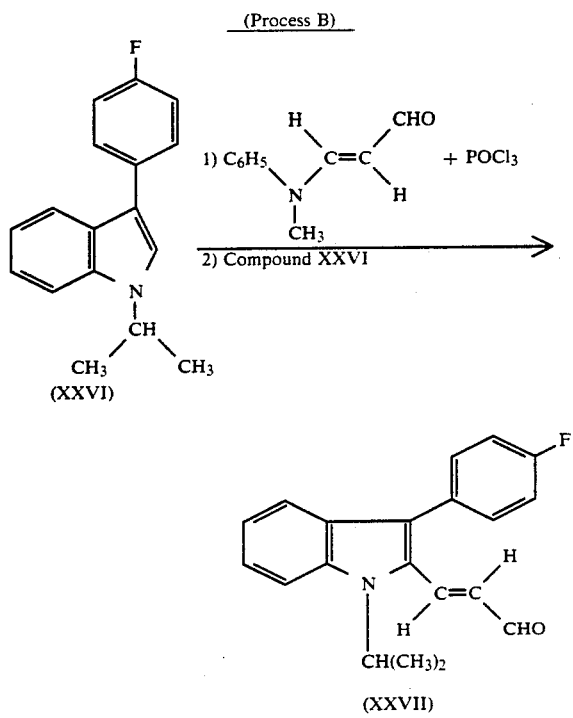

A 5 l. four-neck round bottom flask equipped with a stirrer, condenser, thermometer, addition funnel and cooling bath is charged, under a blanket of dry nitrogen, with 100 ml. of dry acetonitrile and 174.4 g. (1.14 moles) of phosphorus oxychloride, the mixture is cooled to −5° C., and a solution of 184 g. (0.96 mole) of 83.5% pure 3-N-methyl-N-phenylaminoacrolein in 156 ml. of dry acetonitrile is added over a period of 45 minutes while maintaining a temperature of −5°-5° C. The reaction mixture is stirred at 0°-5° C. for 10 minutes, and 115.2 g. (0.45 mole) of 3-(4'-fluorophenyl)-1-(1'-methylethyl)-1H-indole (Compound XXVI) is added over a period of 20 minutes while maintaining a temperature of 0°-5° C. The reaction mixture is refluxed (83° C.) for 9 hours and cooled to 10° C., and a solution of 228 g. (5.7 moles) of sodium hydroxide in 2.0 l. of water is slowly added over a period of 30 minutes while maintaining a temperature of 25°-30° C., the addition being very exothermic. 1.6 l. of toluene is added, the mixture is stirred at 25° C. for 30 minutes and filtered through a filter pad. The filter cake is washed with 100 ml. of toluene, and the washing is combined with the previous filtrate. The organic layer is separated, and a mixture of 93.4 g. of concentrated hydrochloric acid and 2 l. of water is added followed by 400 ml. of saturated sodium chloride solution. The mixture is stirred at 25° C. for 30 minutes, and the resulting slurry is filtered through a filter pad. The tars are washed with 100 ml. of toluene, and the washing is combined with the filtrate. The organic layer is separated, washed twice with 2 l. portions of deionized water and filtered through a filter pad. As much toluene as possible is recovered by distillation at 30-50 mm. Hg and an external temperature of 60°-65° C. to obtain a thick stirrable oil. 100 ml. of 95% ethanol is added, as much ethanol as possible is recovered by distillation at 30-80 mm. Hg and 60°-65° C., and this is repeated twice. 180 ml. Hg of 95% ethanol is added, and the mixture is refluxed (78° C.) for 15 minutes and slowly cooled to 20° C. over a period of 2 hours, crystallization commencing at ∼55° C. The slurry is slowly cooled to 0°-5° C. over a period of 30 minutes, maintained at 0°-2° C. for 1 hour and filtered. The filter cake is washed three times with 50 ml. portions of cold (0°-5° C.) 95% ethanol and vacuum dried at 60°-65° C. for 16 hours to constant weight to obtain the 98 7% pure product (101 g. (71.3%)), m.p. 127°-128° C.

REVISED PROCEDURE:

A 5 l. four-neck round bottom flask equipped with a stirrer, condenser, thermometer, addition funnel and cooling bath is charged, under a blanket of dry nitrogen, with 263 ml. of dry acetonitrile and 454 g. (2.96 moles) of phosphoruside, the mixture is cooled to −5° C., and a solution of 471.6 g. (2.49 moles) of 85.5% pure 3-N-methyl-N-phenylaminoacrolein in 406 ml. of dry acetonitrile is added over a period of 45 minutes while maintaining a temperature of 5°-7° C. The reaction mixture is stirred at 5°-7° C. for 10 minutes and 300 g. (1.18 moles) of Compound XXVI is added over a period of 10 minutes while maintaining a temperature of ∼7° C. The reaction mixture is refluxed (83° C.) for 3 hours and cooled to 22° C., and 2.7 l. of water is slowly added over a period of 15 minutes while maintaining a temperature of 22°-35° C., the addition being exothermic. The reaction mixture is stirred at 35°-50° C. for 30 minutes, heated at 50°-55° C. for 1.5 hours (a longer period of heating may be necessary for complete hydrolysis), cooled to 22° C., maintained at 22° C. for 15 minutes and filtered. The filter cake is washed three times with 600 ml. portions of water and suction dried at aspirator pressure for 6-16 hours. (N-methylaniline may be recovered from the combined aqueous layer and washings.) The wet filter cake is transferred to the original 5 l. flask, 2.5 l. of toluene and 180 g. of 20μ. powdered cellulose are added, and the mixture is heated at 50°-55° for 1.5 hours, cooled to 22° C., maintained at 22° C. for 15 minutes and filtered through a pad of 91 g. of 70-230 mesh A.S.T.M. silica gel covered with a filter cloth. The cellulose and silica gel pad are washed three times with 200 ml. portions of toluene. The toluene filtrate and washings are combined and as much toluene as possible is recovered by distillation at 30-50 mm. Hg and 50°-65° C. (external). 280 ml. of 95% ethanol is added to the residual thick oil, the ethanol is distilled at 20-30 mm. Hg and 60°-65° C., 280 ml. of 95% ethanol is added, and as much ethanol as possible is distilled at 30-80 mm Hg and 60°-65° C. 700 ml. of 95% ethanol is added, and the mixture is refluxed at 78° C. for 15 minutes and slowly cooled to 20° C. over a period of 1 hour, crystallization commencing at ∼55° C. The resulting slurry is cooled to 0°-5° C. over a period of 30 minutes and maintained at 0°-2° C. for 30 minutes, and the solids are collected by filtration, washed three times with 120 ml. portions of cold (0°-5° C.) 95% ethanol and vacuum dried at 60°-65° C. for 16 hours to constant weight to obtain the 99.4% pure product (276.6 g. (75.5%)), m.p. 129°-130° C.

EXAMPLE 7

(E)-3-[3'-(4''-fluorophenyl)-1'-(1''-methylethyl)-1H-indol-2'-yl]prop-2-enal

*(Process AB)*

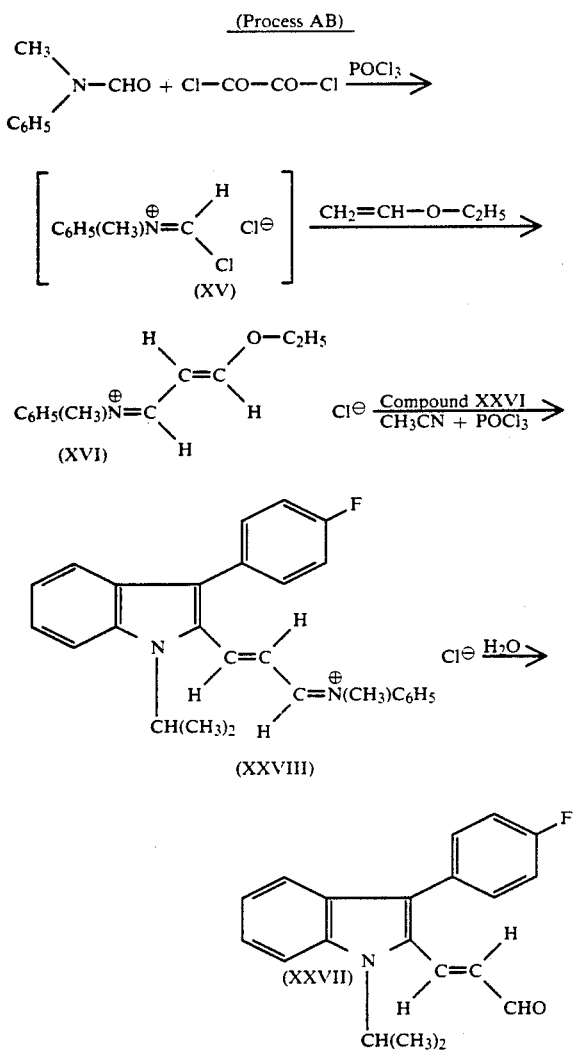

A 5 l. four-neck round bottom flask equipped with a brine-cooled condenser, thermometer, dry nitrogen inlet, mechanical stirrer, cooling bath (−20° C.), addition funnel and caustic scrubber is charged with 480 g. (330 ml., 3.78 moles) of oxalyl chloride and 612 g. (383 ml, 3.99 moles) of phosphorus oxychloride. The mixture is cooled to −10° C., and a cold (0° C.) mixture of 268 g. (355 ml., 3.72 moles) of ethyl vinyl ether and 456 g. (416 ml., 3.37 moles) of N-methylformanilide is slowly added over a 1-1.2 hour period with stirring at −7°-−5° C. to obtain a homogeneous brown-orange mixture, the addition being exothermic and accompanied by the evolution of carbon monoxide and dioxide. The mixture is slowly heated to 35°-40° C. over a 30 minute period and stirred at 40°-45° C. for 30 minutes to obtain a brown homogeneous mixture, most of the unreacted oxalyl chloride and ethyl vinyl ether is distilled at 45°-50° C. and 40-100 mm. Hg over a 30 minute period, and the mixture is cooled to 35°-40° C. 334 g. (1.28 moles) of Compound XXVI and 250 ml. of acetonitrile are separately added at 35°-40° C. with stirring, and the reaction mixture is heated to reflux (~92° C., gentle refluxing commencing at 65° C. with the temperature rising as hydrogen chloride is evolved) over a 30 minute period, gently refluxed for 5 hours to obtain a homogeneous brown solution and cooled to 75° C. 400 ml. of acetonitrile is added with stirring, 2.73 l. of water is slowly added with stirring at 35°-40° C. over a 20 minute period, and the reaction mixture is heated at 50°-55° C. for 1.5 hours, allowed to cool to 22° C. and stirred at this temperature for 16 hours to obtain a dark slurry. The slurry is filtered, and the filter cake is washed four times with 580 ml. portions of water and air dried with suction for 4 hours. The still damp filter cake is transfered to the original reaction vessel, 2.5 l. of toluene and 202 g. of 20µ. cellulose powder are added, and the resulting slurry is heated at 50°-55° C. for 1.5 hours, cooled to 17° C., stirred at this temperature for 25 minutes and filtered through a Buchner funnel containing a filter pad and filter paper. The cellulose bed is washed four times with 150 ml. portions of toluene, and the washings are combined with the original filtrate. The resulting toluene solution is distilled at 50°-60° C. (external) and 30-50 mm. Hg, 167 ml. of 95% ethanol is added with stirring to the resulting dark brown stirrable oil, as much ethanol as possible is distilled at 60°-65° C. (external) and 30-50 mm. Hg, and the addition of 95% ethanol and distillation are repeated two additional times. 756 ml. of 95% ethanol is added to the resulting thick stirrable slurry, the mixture is heated at 78° C. (external) for 15 minutes to obtain a brown solution, and the solution is slowly cooled to 20° C. over a 60 minute period, crystallization commencing at 50°-55° C. The resulting slurry is stirred at 20°-25° C. for 16 hours, and the obtained solid is collected by filtration, washed three times with 136 ml. portions of cold (0° C.) 95% ethanol and vacuum dried at 60°-65° C. for 48 hours to obtain the 93.13% pure product (258 g. (60.93%)), m.p. 124°-126° C.

Throughout the examples, unless otherwise indicated, all temperatures are internal temperatures.

What is claimed is:

1. A process for synthesizing a comopund of the formula

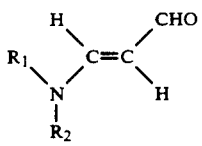

comprising the steps of (i) reacting a compound of the formula

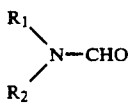

with a compound of the formula

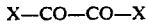

to form the corresponding compound of the formula

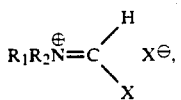

(ii) reacting said compound of the formula

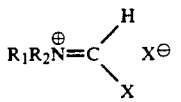

with a compound of the formula

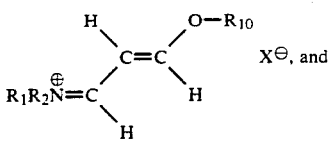

to form the corresponding compound of the formula

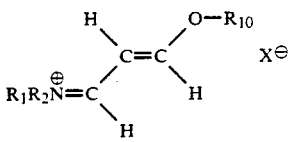

(iii) hydrolyzing said compound of the formula

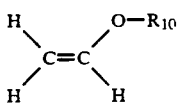

to obtain the corresponding compound of the formula

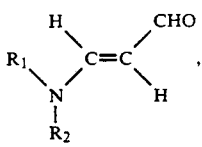

wherein $R_1$ is $C_{1-3}$alkyl, phenyl or phenyl substituted by 1 to 3 substituents each of which is independently $C_{1-3}$alkyl, $C_{1-3}$alkoxy, fluoro, chloro, bromo or nitro (maximum of two nitro groups), $R_2$ is $C_{1-3}$alkyl, $R_{10}$ is $C_{1-6}$alkyl, each X is chloro or bromo, and each $X^{\ominus}$ is chloride or bromide.

2. A process according to claim 1 wherein Steps (i) and (ii) are carried out in inert anhydrous organic media, and Step (iii) is carried out with base.

3. A process according to claim 2 wherein $R_1$ is $C_{1-3}$alkyl.

4. A process according to claim 3 comprising the further step of (iv) treating the crude compound of the formula

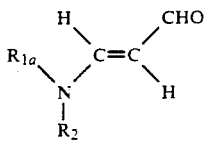

with the corresponding compound of the formula

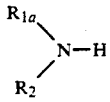

to convert any compound of the formula

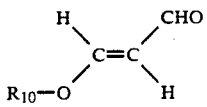

present therein into additional compound of the formula

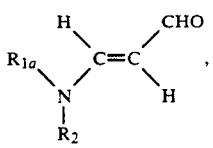

wherein $R_{1a}$ is $C_{1-3}$alkyl.

5. A process according to claim 4 wherein $R_{1a}$ is $C_{1-2}$alkyl, $R_2$ is $C_{1-2}$alkyl, $R_{10}$ is primary or secondary $C_{2-4}$alkyl, each X is chloro, and each $X^{\ominus}$ is chloride.

6. A process according to claim 5 wherein $R_{10}$ is n-$C_{2-4}$alkyl.

7. A process according to claim 6 wherein Steps (i) and (ii) are carried out in a liquid halogenated lower alkane, Step (iii) is carried out in an aqueous medium, and Step (iv) is carried out in a $C_{1-4}$alkanol.

8. A process according to claim 7 wherein Step (i) is carried out in methylene chloride at a temperature of 0°–20° C., Step (ii) is carried out in methylene chloride at a temperature of 25°–40° C., Step (iii) is carried out in water at a temperature of 20°–65C., and Step (iv) is carried out in methanol at a temperature of 10°–20° C.

9. A process according to claim 8 comprising the steps of (i) reacting N,N-dimethylformamide with oxalyl chloride in methylene chloride at a temperature of 0°–15° C. to form the compound of the formula

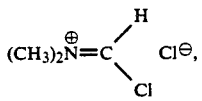

(ii) reacting said compound of the formula

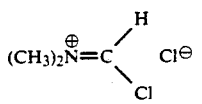

with ethyl vinyl ether in methylene chloride at a temperature of 25°-40° C. to form the compound of the formula

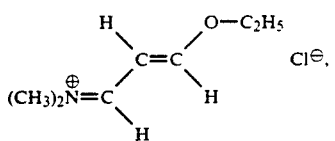

(iii) hydrolyzing said compound of the formula

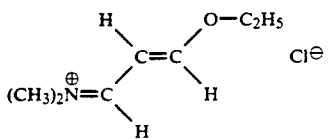

with water at 20°-60° C. and subsequently treating with potassium carbonate in an aqueous medium at a temperature of 20°-30° C. to form a mixture of the compounds of the formulae

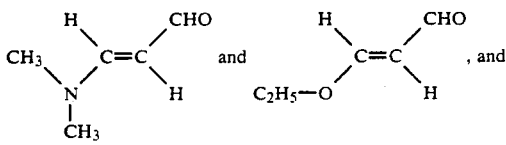

(iv) treating the mixture of the compounds of the formulae

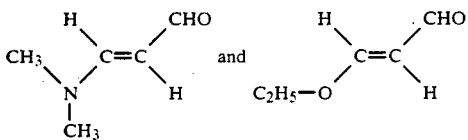

with dimethylamine in methanol at a temperature of 10°-20° C. to convert the compound of the formula

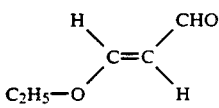

into additional compound of the formula

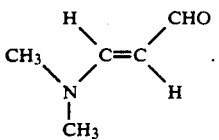

10. A process according to claim 9 wherein (1) the molar ratio of oxalyl chloride to N,N-dimethylformamide in Step (i) is 1–1.2:1, and Step (i) is carried out by adding oxalyl chloride to a solution of N,N-dimethylformamide in methylene chloride over a period of 1.5–4 hours at a rate such that the temperature is maintained at 5°-15° C., (2) in Step (ii) the molar ratio of ethyl vinyl ether to the N,N-dimethylformamide utilized in Step (i) is 1–1.2:1, and Step (ii) is carried out by adding ethyl vinyl ether to the reaction mixture over a period of 0.4–1.5 hours at a rate such that the temperature does not exceed 30° C. and, upon completion of the addition, refluxing the reaction mixture at 35°-40° C. for 0.3–1 hour and recovering as much methylene chloride as possible at a temperature not in excess of 45° C., (3) in Step (iii) the molar ratio of potassium carbonate to the oxalyl chloride utilized in Step (i) is 1–2:1, and Step (iii) is carried out by adding water to the product of Step (ii) stirred at 20°-30° C., allowing the temperature to rise to 45°-60° C., maintaining this temperature during the balance of the addition of the water and for an additional 0.3–1 hour, cooling the reaction mixture to 15°-25° C., adding an aqueous solution of potassium carbonate over a period of 0.3–1.25 hours at this temperature, extracting the mixture with methylene chloride and distilling as much methylene chloride as possible at a temperature not in excess of 45° C., and (4) in Step (iv) the molar ratio of dimethylamine to the N,N-dimethylformamide utilized in Step (i) is 0.15–0.4:1, and Step (iv) is carried out by adding anhydrous dimethylamine to a solution of the product of Step (iii) in methanol stirred at 10°-20° C. at a rate such that the temperature does not exceed 20° C. and distilling the solvent and any excess dimethylamine at a temperature not in excess of 120° C.

11. A process according to claim 2 wherein $R_1$ is phenyl or phenyl substituted by 1 to 3 substituents each of which is independently $C_{1-3}$alkyl, $C_{1-3}$alkoxy, fluoro, chloro, bromo or nitro (maximum of two nitro groups).

12. A process according to claim 11 wherein $R_1$ is phenyl or phenyl substituted by 1 or 2 substituents each of which is independently $C_{1-3}$alkyl, $C_{1-2}$alkoxy or chloro, $R_2$ is $C_{1-2}$alkyl, $R_{10}$ is primary or secondary $C_{2-4}$alkyl, each X is chloro, and each $X^\ominus$ is chloride.

13. A process according to claim 12 wherein $R_1$ is phenyl or phenyl substituted by 1 or 2 methyl groups, and $R_{10}$ is n-$C_{2-4}$alkyl.

14. A process according to claim 13 wherein $R_1$ is phenyl, $R_2$ is methyl, and $R_{10}$ is ethyl or n-butyl.

15. A process according to claim 13 wherein Steps (i) and (ii) are carried out in a liquid halogenated lower alkane or acetonitrile, and Step (iii) is carried out in a mixture of water and a liquid halogenated lower alkane or acetonitrile.

16. A process according to claim 15 wherein Step (i) is carried out prior to Step (ii), Step (i) is carried out in methylene chloride or acetonitrile at a temperature of −20°-45° C., Step (ii) is carried out in methylene chloride or acetonitrile at a temperature of 10°-40° C., and Step (iii) is carried out in a mixture of water and either methylene chloride or acetonitrile at a temperature of 0°-35° C.

17. A process according to claim 16 comprising the steps of (i) reacting N-methylformanilide with oxalyl chloride in methylene chloride at a temperature of 15°-45° C. to form the compound of the formula

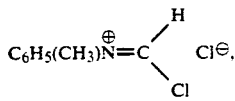

(ii) reacting said compound of the formula

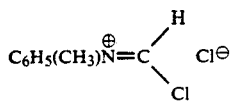

with ethyl vinyl ether in methylene chloride at a temperature of 15°–40° C. to form the compound of the formula

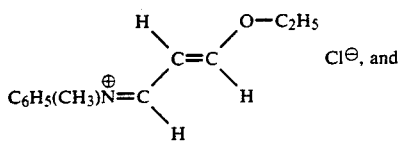

(iii) hydrolyzing said compound of the formula

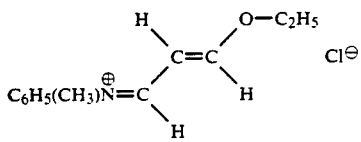

with sodium carbonate in a mixture of methylene chloride and water at a temperature of 20°–30° C. to obtain the compound of the formula

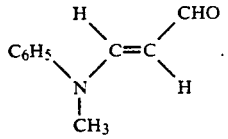

18. A process according to claim 17 wherein (1) the molar ratio of oxalyl chloride to N-methylformanilide in Step (i) is 1–1.2:1, and Step (i) is carried out by adding oxalyl chloride to a solution of N-methylformanilide in methylene chloride at 15°–20° C. over a period of 1–2 hours and, upon completion of the addition, gradually raising the temperature of the reaction mixture to 40°–45° C. over a period of 0.75–1.25 hours and then refluxing it for 0.75–1.25 hours, (2) in Step (ii) the molar ratio of ethyl vinyl ether to the N-methylformanilide utilized in Step (i) is 1–1.3:1, and Step (ii) is carried out by cooling the product of Step (i) to 15°–20° C., adding ethyl vinyl ether over a period of 0.5–1.5 hours at a rate such that the temperature does not exceed 30° C., and, upon completion of the addition, refluxing the reaction mixture for 0.3–0.7 hour, and (3) in Step (iii) the molar ratio of sodium carbonate to the oxalyl chloride utilized in Step (i) is 1–1.2:1, and Step (iii) is carried out by cooling the product of Step (ii) to 15°–20° C., adding, over a period of 0.5–1 hour, an aqueous solution of sodium carbonate at a rate such that the temperature of the reaction mixture is 20°–30° C. and, upon completion of the addition, stirring the mixture at 20°–30° C. for 0.2–0.5 hour, allowing the mixture to separate into two phases, separating the two phases and recovering the product from the organic phase.

19. A process according to claim 16 comprising the
(i) reacting N-methylformanilide with oxalyl chloride in acetonitrile at a temperature of −20°–20° C. to form the compound of the formula

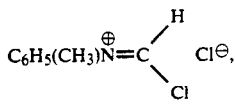

(ii) reacting said compound of the formula

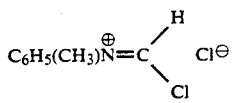

with n-butyl vinyl ether in acetonitrile at a temperature of 10°–40° C. to form the compound of the formula

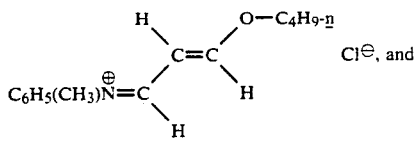

(iii) hydrolyzing said compound of the formula

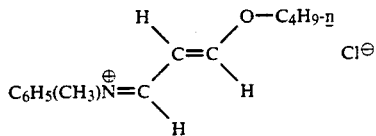

with sodium carbonate in a mixture of acetonitrile and water at a temperature of 0°–25° C. to obtain the compound of the formula

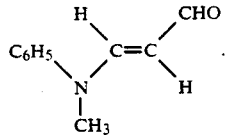

20. A process according to claim 19 wherein (1) the molar ratio of oxalyl chloride to N-methylformanilide in Step (i) is 1–1.2:1, and Step (i) is carried out by adding oxalyl chloride to a solution of N-methylformanilide in acetonitrile at −18°–8° C. over a period of 1–2 hours and, upon completion of the addition, gradually raising the temperature of the reaction mixture to 12°–20° C. over a period of 0.4–0.75 hour and then stirring it for 0.2–0.4 hour at this temperature, (2) in Step (ii) the molar ratio of n-butyl vinyl ether to the N-methylformanilide utilized in Step (i) is 1–1.2:1, and Step (ii) is carried out by adding n-butyl vinyl ether to the product of Step (i) stirred at 12°–20° C. over a period of 0.5–1.5 hours at a rate such that the temperature does not exceed 30° C., and, upon completion of the addition, stirring the reaction mixture for 0.3–0.7 hour at 25°–35° C., and (3) in Step (iii) the molar ratio of sodium carbonate to the oxalyl chloride utilized in Step (i) is 1–1.3:1, and Step (iii) is carried out by cooling the product of Step (ii) to 0°–5° C. adding, over a period of 0.5–1.2 hours, an aqueous solution of sodium carbonate at a rate such that the temperature of the reaction mixture is 5°–12° C. and, upon completion of the addition, adding toluene, stirring the mixture at 15°–25° C. for 0.2–0.5 hour, allowing the mixture to separate into two phases, separating the two phases and recovering the product from the organic 21. A process according to claim 15 wherein Steps (i) and (ii) are carried out simultaneously in methylene chloride or acetonitrile at a temperature of −15°–35° C., and Step (iii) is carried out in a mixture of water and either methylene chloride or acetonitrile at a temperature of 0°–35° C.

22. A process according to claim 21 comprising the
(i) and (ii) reacting N-methylformanilide with oxalyl chloride in acetonitrile at −10°–−30° C. in the presence of n-butyl vinyl ether to form the compound of the formula

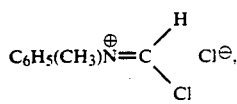

which compound then reacts with the n-butyl vinyl ether in the reaction mixture to form the compound of the formula

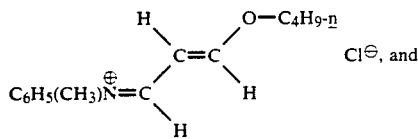

(iii) hydrolyzing said compound of the formula

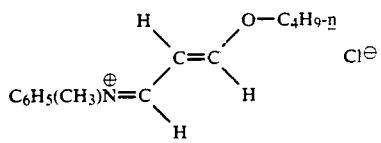

with sodium carbonate in a mixture of acetonitrile and water at a temperature of 0°–25° C. to obtain the compound of the formula

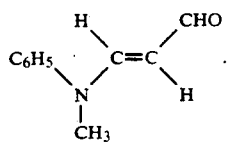

23. A process according to claim 22 wherein (1) in Steps (i) and (ii), the molar ratio of oxalyl chloride and n-butyl vinyl ether to N-methylformanilide is 1–1.2:1–1.2:1, and Steps (i) and (ii) are carried out by adding a solution of N-methylformanilide and n-butyl vinyl ether in acetonitrile to a solution of oxalyl chloride in acetonitrile stirred at −10°–10° C. over a period of 2–3 hours and, upon completion of the addition, gradually raising the temperature of the reaction mixture to 20°–30° C. over a period of 0.4–1.5 hours and then stirring the reaction mixture at this temperature for 0.5–1.5 hours, and (2) in Step (iii) the molar ratio of sodium carbonate to the oxalyl chloride utilized in Step (i) is 1–1.3:1, and Step (iii) is carried out by cooling the product of Step (ii) to 0°–5° C., adding, over a period of 0.5–1.2 hours, an aqueous solution of sodium carbonate at a rate such that the temperature of the reaction mixture is 0°–12° C. and, upon completion of the addition, adding toluene, stirring the mixture at 15°–25° C. for 0.2–0.5 hour, allowing the mixture to separate into two phases, separating the two phases and recovering the product from the organic phase.

* * * * *